(12) United States Patent
Carreel et al.

(10) Patent No.: US 9,778,095 B2
(45) Date of Patent: Oct. 3, 2017

(54) MULTIPURPOSE WEIGHING DEVICE

(71) Applicant: WITHINGS, Issy les Moulineaux (FR)

(72) Inventors: Eric Carreel, Meudon (FR); Brice Brac De La Perriere, Paris (FR); Nadine Buard, Meudon (FR); Pierre Barrochin, Saint Cloud (FR); Rui-Yi Yang, Auxerre (FR); Guillaume Faussard, Villiers-le-Mahieu (FR); Said Aitmbarek, Antony (FR)

(73) Assignee: Withings

( * ) Notice: Subject to any disclaimer, the term of this patent is extended or adjusted under 35 U.S.C. 154(b) by 109 days.

(21) Appl. No.: 14/759,065

(22) PCT Filed: Dec. 30, 2013

(86) PCT No.: PCT/FR2013/053280
§ 371 (c)(1),
(2) Date: Jul. 2, 2015

(87) PCT Pub. No.: WO2014/106716
PCT Pub. Date: Jul. 10, 2014

(65) Prior Publication Data
US 2015/0338265 A1    Nov. 26, 2015

(30) Foreign Application Priority Data
Jan. 2, 2013  (FR) ..................... 13 50013

(51) Int. Cl.
*G01G 19/414*  (2006.01)
*G01G 19/50*   (2006.01)
*A61B 5/0245*  (2006.01)
*A61B 5/053*   (2006.01)
*A61B 5/024*   (2006.01)

(52) U.S. Cl.
CPC ............ *G01G 19/50* (2013.01); *A61B 5/024* (2013.01); *A61B 5/0537* (2013.01); *G01G 19/4144* (2013.01)

(58) Field of Classification Search
CPC . A61B 5/024; A61B 5/02438; A61B 5/02444; A61B 5/0255; A61B 5/0537; A61B 5/1102; A61B 5/6829; G01G 19/50; G01G 19/4144
See application file for complete search history.

(56) References Cited

U.S. PATENT DOCUMENTS 3,906,931 A * 9/1975 Terekhov ............. A61B 5/1036
                                                    600/595
4,433,741 A * 2/1984 Ryckman, Jr. ....... G01G 3/1402
                                                    177/199

(Continued)

*Primary Examiner* — Randy Gibson
(74) *Attorney, Agent, or Firm* — Miller, Matthias & Hull LLP

(57) ABSTRACT

Weighing device of the digital bathroom scale type, comprising four feet each having a strain gauge, four conducting portions on the top surface, and one electronic control unit, the electronic unit being configured to measure first signals indicative of periodic variations in weight and second signals indicative of periodic variations in impedance caused by the heartbeats of the user, the electronic unit being configured to determine the heart rate of the user from the first and second signals. Method for determining the heart rate of the user from the first and second signals.

11 Claims, 4 Drawing Sheets

(56) References Cited

U.S. PATENT DOCUMENTS

| | | | | |
|---|---|---|---|---|
| 4,556,115 A * | 12/1985 | Lockery | | G01G 3/142 |
| | | | | 177/211 |
| 4,800,973 A * | 1/1989 | Angel | | G01G 19/44 |
| | | | | 177/210 C |
| 4,993,506 A * | 2/1991 | Angel | | G01G 19/44 |
| | | | | 177/211 |
| 5,415,176 A * | 5/1995 | Sato | | A61B 5/0537 |
| | | | | 177/245 |
| 5,620,003 A * | 4/1997 | Sepponen | | A61B 5/024 |
| | | | | 600/527 |
| 5,886,302 A * | 3/1999 | Germanton | | G01G 19/44 |
| | | | | 174/135 |
| 6,354,996 B1 * | 3/2002 | Drinan | | A61B 5/0537 |
| | | | | 128/903 |
| 6,679,854 B2 * | 1/2004 | Honda | | A61B 5/0537 |
| | | | | 177/25.19 |
| 6,782,340 B1 * | 8/2004 | Komatsu | | A61B 5/0537 |
| | | | | 177/246 |
| 8,540,651 B2 * | 9/2013 | Pfeffer | | A61B 5/11 |
| | | | | 600/595 |
| 8,858,449 B2 * | 10/2014 | Inan | | A61B 5/029 |
| | | | | 600/481 |
| 8,870,780 B2 * | 10/2014 | Inan | | A61B 5/029 |
| | | | | 600/481 |
| 8,983,854 B2 * | 3/2015 | Park | | A61B 5/0205 |
| | | | | 600/300 |
| 9,011,346 B2 * | 4/2015 | Wiard | | A61B 5/02125 |
| | | | | 600/508 |
| 9,055,871 B2 * | 6/2015 | Inan | | A61B 5/029 |
| 9,215,991 B2 * | 12/2015 | Inan | | A61B 5/029 |
| 2004/0251057 A1 * | 12/2004 | Suzuki | | A61B 5/0537 |
| | | | | 177/25.13 |
| 2006/0096789 A1 * | 5/2006 | Kenmochi | | A61B 5/0537 |
| | | | | 177/25.13 |
| 2010/0094147 A1 * | 4/2010 | Inan | | A61B 5/7207 |
| | | | | 600/500 |
| 2010/0156598 A1 * | 6/2010 | Leung | | A61B 5/0002 |
| | | | | 340/10.1 |
| 2010/0210921 A1 * | 8/2010 | Park | | A61B 5/0205 |
| | | | | 600/301 |
| 2012/0071792 A1 * | 3/2012 | Pfeffer | | A61B 5/11 |
| | | | | 600/587 |
| 2014/0142437 A1 * | 5/2014 | Inan | | A61B 5/7207 |
| | | | | 600/479 |
| 2015/0073234 A1 * | 3/2015 | Inan | | A61B 5/7207 |
| | | | | 600/301 |
| 2015/0112209 A1 * | 4/2015 | Blaber | | A61B 5/7246 |
| | | | | 600/483 |
| 2015/0160068 A1 * | 6/2015 | Carreel | | G01G 3/1404 |
| | | | | 177/1 |
| 2015/0257680 A1 * | 9/2015 | Inan | | A61B 5/7207 |
| | | | | 600/301 |
| 2015/0359441 A1 * | 12/2015 | Giovangrandi | | A61B 5/0295 |
| | | | | 600/509 |
| 2015/0359452 A1 * | 12/2015 | Giovangrandi | | A61B 5/0295 |
| | | | | 600/547 |
| 2015/0359486 A1 * | 12/2015 | Kovacs | | A61B 5/0245 |
| | | | | 600/301 |
| 2016/0022156 A1 * | 1/2016 | Kovacs | | A61B 5/0245 |
| | | | | 600/483 |
| 2016/0095521 A1 * | 4/2016 | Inan | | A61B 5/7207 |
| | | | | 600/301 |
| 2016/0095522 A1 * | 4/2016 | Wiard | | A61B 5/02125 |
| | | | | 600/483 |
| 2016/0174852 A1 * | 6/2016 | He | | A61B 5/7278 |
| | | | | 600/301 |
| 2016/0317043 A1 * | 11/2016 | Campo | | A61B 5/0205 |
| 2016/0374618 A1 * | 12/2016 | Giovangrandi | | A61B 5/6887 |
| | | | | 600/393 |

* cited by examiner

MULTIPURPOSE WEIGHING DEVICE

CROSS-REFERENCE TO RELATED APPLICATIONS

This application is a 35 USC §371 U.S. national stage filing of International Patent Application No. PCT/FR2013/053280 filed on Dec. 30, 2013, which claims priority under the Paris Convention and 35 USC §119 to French Patent Application No. 13 50013, filed on Jan. 2, 2013.

FIELD OF THE DISCLOSURE

The present invention relates to weighing devices and methods.

BACKGROUND OF THE DISCLOSURE

More particularly, the invention relates to the field of digital bathroom scales. These devices are usually equipped with four feet, each foot being provided with a strain gauge. It has been proposed to use said strain gauges to measure the heart rate (pulse) of a user positioned on the scale, for example in document ES2328205. However, it has been found that this method works for some of the population but does not work for a significant proportion of individuals in the population.

Some digital bathroom scales provide an impedance measurement function, for example to indicate a physiological index of the user such as the body fat percentage. This requires the user to stand barefoot on the scale, however. It has been proposed to use the impedance measurement to assess the user's heart rate, for example in document ES2296474. However, again it has been found that this method can work for some of the population but does not work for a significant proportion of individuals in the population, and in addition the user must be barefoot.

There is therefore a need to provide an improved solution for measuring the heart rate of an individual positioned on a digital scale.

SUMMARY OF THE DISCLOSURE

To this end, the invention proposes a digital bathroom scale comprising at least one strain gauge, at least two conducting portions arranged on a top surface, and an electronic control unit,
the strain gauge being connected to the electronic unit and the electronic unit being configured to determine the weight of a user positioned on the weighing device, and to measure a first signal indicative of the periodic variations in weight caused by the heartbeats of the user, the conducting portions being connected to the electronic unit and the electronic unit being configured to measure an impedance at the terminals of the user's feet and to measure a second signal indicative of the periodic variations in impedance caused by the heartbeats of the user,
characterized in that the electronic unit is configured to perform a qualitative individual analysis of the first and second signals and a comparative analysis of the first and second signals so as to determine from the first and second signals the heart rate of the user, so that the measurement and display of the heart rate are made more reliable by the combined analysis of the two signals.

With these arrangements, a more reliable measurement of the heart rate of an individual is obtained, which allows measuring the heart rate for most individuals.

In embodiments of the method according to the invention, one or more of the following arrangements may possibly be used:

The device may comprise four conducting portions, and the electronic unit may be configured to inject a modulated or pulsed current between two of the conducting portions and to measure the electric potential difference between the two other conducting portions, in order to determine the variations in electric potential difference and thus determine the cardiac second signal; thereby preventing the electrical impulses from muscles from causing interference in the cardiac second signal, and making the impedance measurement more reliable without the average injected current being too high.

The electronic unit may be configured to evaluate a quality index for the first signal and a quality index for the second signal, and to determine the heart rate from the signal having the best quality index; whereby the most appropriate among first and second signals can always be selected to determine the heart rate.

The electronic unit may be configured to perform a cross-correlation calculation on the first and second signals; whereby the first and second signals can advantageously be combined.

The electronic unit may be configured to measure a phase difference between the first and second signals, and to shift the second signal relative to the first signal by said phase difference; in this manner, the cross-correlation calculation eliminates noise and maximizes the useful signal portions.

The electronic unit may be configured to evaluate a quality index for the cross-correlation calculation, and to determine the heart rate from the first and second signals and from the cross-correlation calculation by choosing the one of the three that has the highest quality index; whereby the measurement coverage rate is maximized to cover most individuals.

The device may comprise four feet and four corresponding strain gauges, combined into two Wheatstone bridges, to allow the electronic unit to measure a user's weight and weight variations; whereby the weighing scheme is optimized and the weight measurement is made more reliable.

The invention also provides a method implemented in a digital bathroom scale comprising at least one strain gauge, at least two conducting portions arranged on a top surface, and an electronic control unit, the strain gauge and the conducting portions being connected to the electronic unit to enable the electronic unit to measure the weight of a user positioned on the weighing device and an impedance at the terminals of the user's feet, the method comprising the steps of:

a—measuring a first signal indicative of the periodic variations in weight caused by the heartbeats of the user, b—measuring a second signal indicative of the periodic variations in impedance caused by the heartbeats of the user, c0—performing a qualitative individual analysis of the first and second signals and a comparative analysis of the first and second signals, c—determining the heart rate of the user from the first and second signals, so that the measurement and display of the heart rate are made more reliable by the combined analysis of the two signals.

The device may comprise four conducting portions, said method then comprising, during step b-, injecting a pulsed current between two of the conducting portions and measuring the electric voltage difference between the two other conducting portions, in order to determine the variations in electric potential difference and thus determine the second signal; so that the impedance measurement is made more reliable without the average injected current being too high.

The method may further comprise, in step c-, performing at least one cross-correlation calculation on the first and second signals; whereby the first and second signals can advantageously be combined.

The method may further comprise, in step c, measuring a phase difference between the first and second signals, in order to shift the second signal relative to the first signal by said phase difference, so that the cross-correlation calculation eliminates noise and maximizes the useful signal portions.

Other features and advantages of the invention will be apparent from the following description of one of its embodiments, given by way of non-limiting example with reference to the accompanying drawings.

BRIEF DESCRIPTION OF THE DRAWINGS

In the drawings.

In the various figures, the same references designate identical or similar elements.

DETAILED DESCRIPTION OF THE DISCLOSURE

Figure 1:
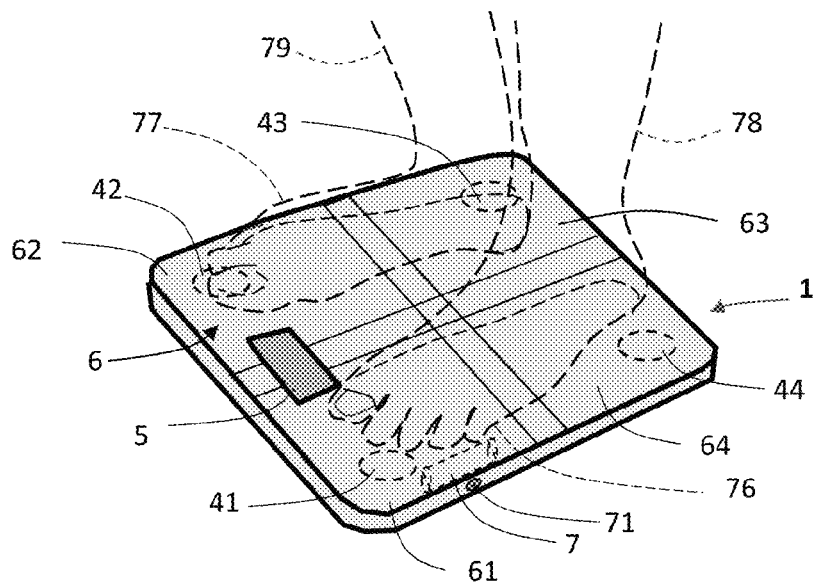
FIG. 1 is a general perspective view of the weighing device according to the invention.

FIG. 1 shows an example of a digital scale 1 (also known as 'bathroom scale') on which a user can stand in order to measure his or her weight. In the example shown, the legs 78,79 of the user are visible, as are the feet 76,77 which are illustrated as bare.

The digital scale 1 comprises a main body that is generally rectangular or square in shape, and four feet 41-44 respectively arranged near the four corners of the body, each foot comprising measurement means.

More specifically, in the example shown here the left front foot 41 comprises a left front strain gauge 31, the right front foot 42 comprises a right front strain gauge 32, the right rear foot 43 comprises a right rear strain gauge 33, and the left rear foot 44 comprises a left rear strain gauge 34.

It is understood that the digital scale could also have a different number of strain gauges, without a direct relation to the number of feet. In particular, there could be only one central strain gauge, or two strain gauges, or even three strain gauges. It is also not excluded to have more than four strain gauges.

Figure 2:
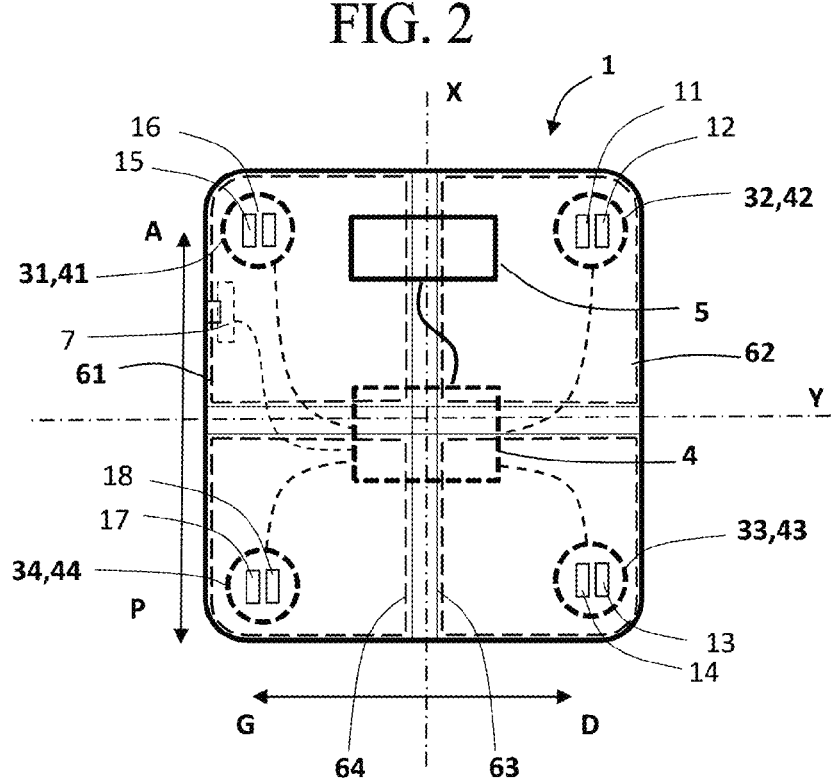
FIG. 2 is a schematic top view of the device of FIG. 1.

In FIG. 2, the front-rear direction is indicated by the X axis, the letter A representing the front and the letter P indicating the rear, while the right-left direction is indicated by the Y axis, extending between the left side denoted G and the right side denoted D.

The digital scale 1 further comprises an electronic control unit 4 (also referred to herein as an 'electronic unit') and a display 5 which will be discussed in more detail below.

The aforementioned strain gauges 31-34 (also known as load sensors) each comprise a first element whose resistance increases under a vertical compression applied to the feet concerned and a second element whose resistance decreases under said vertical compression.

In the example illustrated here, the right front gauge 32 comprises a first such element 11, called the first right front gauge resistor 11, and a second such element, called the second right front gauge resistor 12.

Similarly, the right rear gauge 33 comprises a first such element, called the first right rear gauge resistor 13, and a second such element, called the second right rear gauge resistor 14.

Similarly on the left side, the left front gauge 31 comprises a first such element 15, called the first left front gauge resistor 15, and a second such element, called the second left front gauge resistor 16.

Finally, the left rear gauge 34 comprises a first such element, called the first left rear gauge resistor 17, and a second such element, called the second left rear gauge resistor 18.

Each of the resistors 11-18 respectively has a resistance value denoted R1-R8. In the example shown here, the resistance of the odd resistors increases with the force applied to the feet, while, conversely, that of the even resistors (12,14,16,18) decreases with the force applied.

The combination of the eight resistors 11-18 can take many forms; only one will be detailed below, but other combinations are of course possible.

In addition, the digital scale 1 has a top surface comprising four conducting portions 61-64 arranged on said top surface which are electrically insulated from each other.

These conducting portions serve as electrodes in contact with the user's feet. In a simplified version there may be only two conducting portions, in which case a current is injected between these two portions and an electric potential difference is measured between these same two portions; the example illustrated in the figures, however, is based on a configuration with four conducting portions 61-64.

The left front conducting portion 61 is intended to come into contact with the front of the user's left foot 76; the right front conducting portion 62 is intended to come into contact with the front of the right foot 77; the right rear conducting portion 63 is intended to come into contact with the heel of the right foot 77; the left rear conducting portion 64 is intended to come into contact with the heel of the user's left foot 76. The reverse configuration is also possible but less favorable.

Lastly, the digital scale 1 is equipped with a sensor 7 for reading the carbon dioxide concentration (CO2).

The display 5 comprises a central area where the estimated weight of the person on the scale 1 is displayed. In addition, an auxiliary area is used to display auxiliary information such as the heart rate (HR) or carbon dioxide level (CO2) as will be described below.

Figure 3:
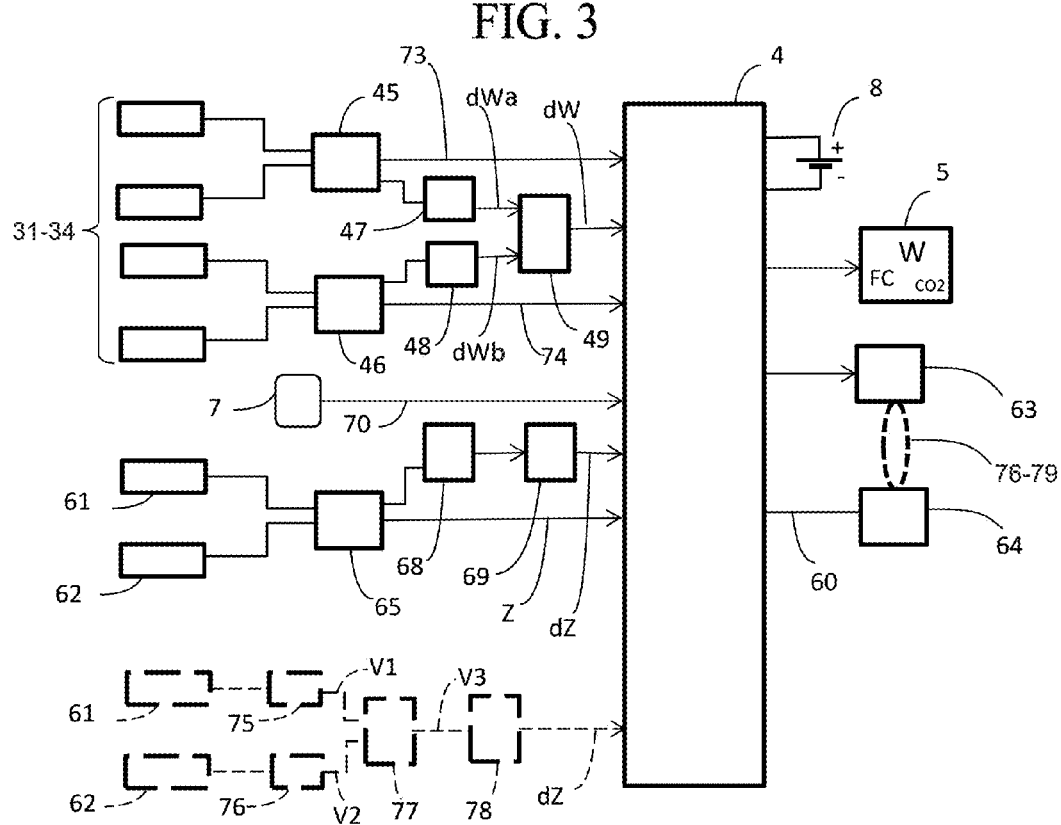
FIG. 3 shows a block diagram for the weighing device of FIG. 1.
Figure 4:
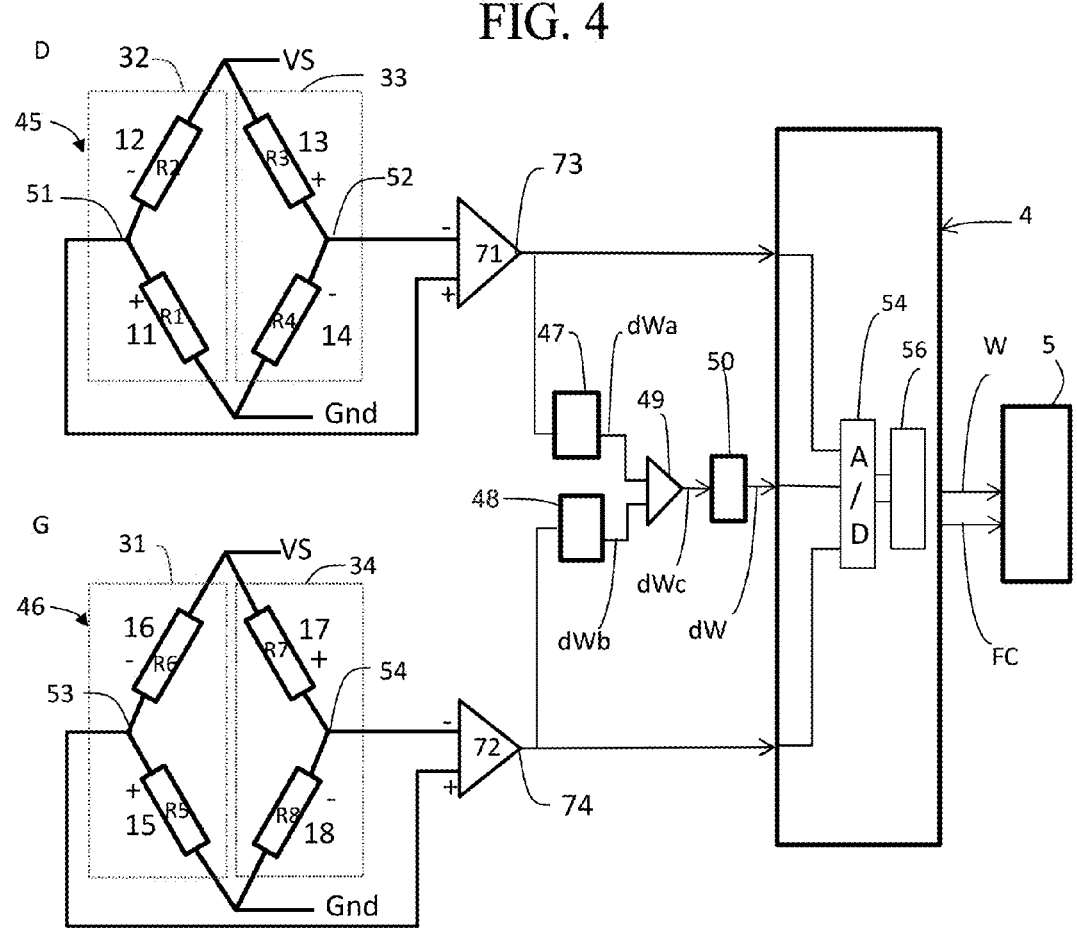
FIG. 4 shows a circuit diagram for the weighing device of FIG. 1.

In FIG. 3, the strain gauges 31-34 are connected to the electronic control unit 4 by means of two Wheatstone bridges 45,46 which are detailed in FIG. 4. Each of the outputs 73,74 from the Wheatstone bridges is then sent to the electronic control unit 4, where they are converted into digital values by an analog-to-digital converter 54 and then summed by an adder circuit 56. The resulting total weight W is displayed on the display 5.

Figure 8:
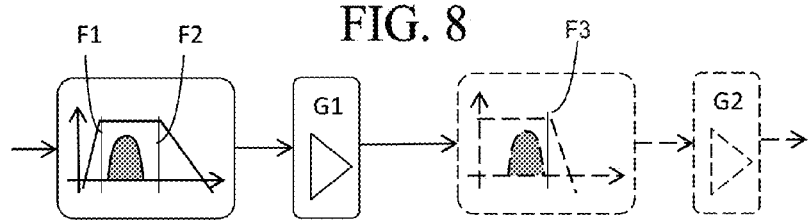
FIG. 8 shows a block diagram of a filtering and amplifying circuit.

Besides, the outputs 73,74 from the Wheatstone bridges 45,46, each respectively, enter a filtering and amplification circuit 47,48 detailed in the block diagram in FIG. 8. The output dWa from the first filtering circuit 47 and the output dWb from the second filtering circuit 48 are summed by an adder assembly 49 which outputs a signal dWc which passes through an amplifier circuit 50, which in turn outputs the signal denoted dW which represents a first signal indicative of the periodic variations in weight caused by the heartbeats of the user.

In addition, the electronic unit is powered by a battery 8 of a conventional type.

In addition, the control unit is connected to one of the rear conducting portions 63 for injecting current into one of the user's feet, said current flowing through the legs 78,79 and body of the user to return through the other foot to the other conducting portion 64 which is connected to the ground 60 of the electronic unit.

The two other (front) conducting portions 61 and 62 are respectively in electrical contact with the front portions of the user's feet, an electric voltage difference indicative of the impedance of the body just acquired at the terminals of said feet by means of a differential circuit 65. This differential circuit 65 outputs a signal Z indicative of the measured impedance of the user's body. A second filtering and amplification circuit 68 eliminates the continuous component of the impedance signal Z to filter and amplify 69 the variations of the impedance signal, which yields the signal denoted dZ that represents a second signal indicative of the periodic variations in impedance caused by the heartbeats of the user.

The electronic unit is configured to determine, from the first signal dW and the second signal dZ, the heart rate of the user, denoted 'HR', which can be displayed on the display 5.

The impedance measurement Z can be obtained by injecting a predetermined current between the conducting portions 63,64.

This current may be fixed, or preferably pulsed or modulated. FIG. 3 illustrates the analog processing to obtain dZ prior to its digital processing.

Figure 5:
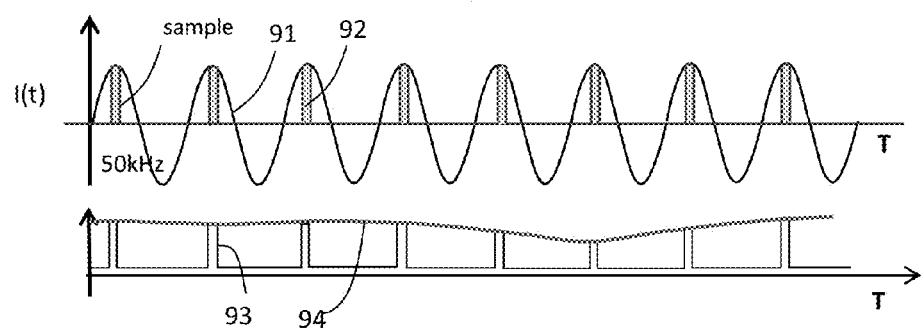
FIG. 5 shows a timing diagram relating to the method for measuring impedance variations.

Advantageously, an alternating signal may be injected as is illustrated in FIG. 5. In this case, the average current injected into the individual positioned on the scale is zero. In the example shown, the current profile 91,I(t) is sinusoidal with a frequency of 50 kHz and a peak current not exceeding 1 milliampere. The current can be supplied by a defined alternate current source, or a peak-to-peak voltage may be applied.

According to a preferred processing, preferably digital, the voltage is sampled at the terminals of the conducting portions 61,62 during a relatively short time corresponding to the peak of the positive half of the wave. The circuit 65 thus can collect samples by periodically sampling measurements 92 indicative of the impedance Z of the individual. In the example shown, the signal is sampled for 2 microseconds, with the period of the control signal being 20 microseconds.

An extrapolation of the sampled points 93 yields a curve 94 corresponding to the measured impedance over time.

In an alternative embodiment represented with a dotted line in FIG. 3, each of voltages sampled in the conducting portions 61,62 is first processed separately by a respective band-pass circuit 75,76. Circuit 75 also comprises an amplification function and outputs a first signal V1 indicative of the voltage variations at terminal 61. In the same manner, the second circuit 76 delivers a second signal V2 indicative of voltage variations at terminal 62. A differentiator circuit 77 subtracts the two voltages V1, V2, and provides an output V3 which is amplified by a filtering and amplification circuit 78 having a block diagram of the type represented in FIG. 8. The second signal dZ representing the periodic variations in the impedance is obtained as output from circuit 78, then converted to digital.

FIG. 4 shows details of the circuit diagram relating to measurement of the weight and its variations. A first Wheatstone bridge 45 combines resistors 11 and 12 of the right front strain gauge 32 and resistors 13 and 14 of the right rear strain gauge 33. A first comparator 71 formats the electric potential difference between the intermediate points 51 and 52 of the first Wheatstone bridge and provides an output 73 indicative of the weight present on the right side of the scale.

A second Wheatstone bridge 46 combines resistors 15 and 16 of the left front strain gauge 31 and resistors 17 and 18 of the left rear strain gauge 34. A second comparator 72 formats the electric potential difference between the intermediate points 53 and 54 of the second Wheatstone bridge and provides an output 74 indicative of the weight present on the left side of the scale.

The strain gauges 31-34 could of course be combined in a front-rear logic instead of a left-right logic. The fact that several analog inputs are fed to the control unit allows indicating a possible misalignment ('off-center') to the user. It is possible to indicate a front-rear misalignment or a left-right misalignment, or even a more precise indication as disclosed in patent application FR1256995 (patent publication FR2993654) from the same applicant.

The partial weight signals 73,74 are summed by the adder circuit which outputs an analog signal W indicative of the total weight of the user. Also, this signal W can enter a filtering and amplification circuit like 48 mentioned above. It outputs a signal dW (mentioned above) indicative of the weight variations.

In FIG. 8, the structure and operation of a filtering and amplification circuit of the type described with reference to circuits 48 and 68 are described.

A first filter that is essentially a band-pass filter eliminates the continuous component of the signal; typically an assembly with a serially connected capacitor is used. The lower cutoff frequency F1 may be between 0.5 Hz and 2 Hz for example. This first filter also optionally includes an upper cutoff frequency F2, preferably greater than 500 Hz.

This first filter is cascaded to a first amplifier stage G1, with a gain of between 50 and 2000. Downstream of this first amplifier stage, a second, low-pass filter with an upper cutoff frequency F3 which may be between 10 Hz and 20 Hz may optionally be provided. Downstream of the second filter, a second amplifier stage G2 may optionally be provided with a gain of between 10 and 100.

Such a filtering and amplification circuit is a very satisfactory way to eliminate the continuous component and the noise and other interference at frequencies above the spectral components normally expected for the signals for variations in weight and/or impedance caused by heartbeats.

Figure 6:
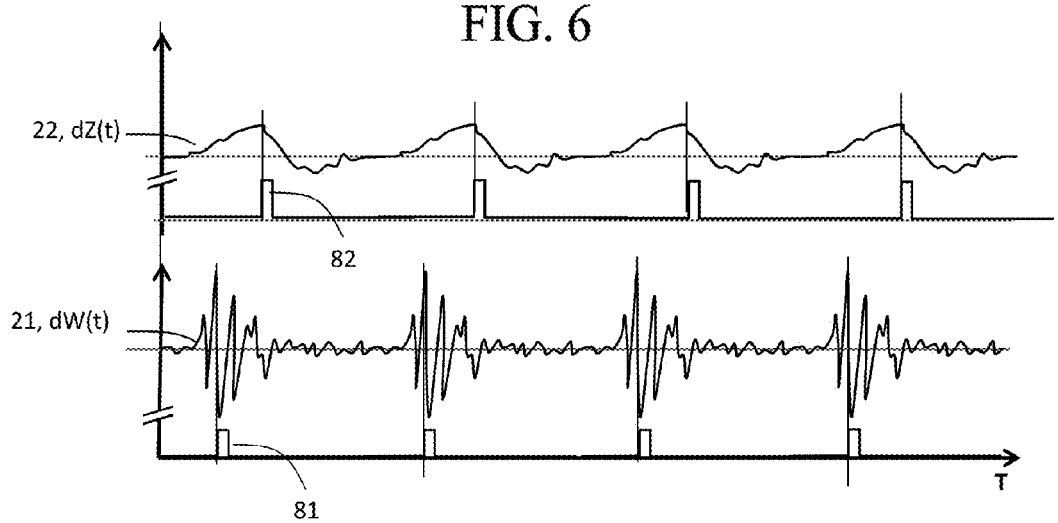
FIGS. 6 and 7 show timing diagrams for the first and second signals.

According to one relatively simple implementation of the method, illustrated in FIG. 6, the first signal 21,W(t) indicative of the periodic variations in weight caused by the user's heartbeats is analyzed by the control unit, which identifies the periodic maxima in order to derive a first pulse signal 81.

In a similar manner, the control unit analyzes the second signal 22,Z(t) indicative of the impedance variations in order to extract the periodic maxima, in order to derive a second pulse signal 82.

For the first signal, the control unit establishes a quality index for the signal, for example the amplitude of the extrema compared to an average standard deviation of the signal, or the median of the time interval between the extrema and/or the standard deviation of the time interval between the extrema, or any other characteristic representing an image of the signal-to-noise ratio. Individual analysis of the first signal 21 yields a quality factor denoted FS1.

The control unit does the same for the second signal to establish a quality index for the second signal. Individual analysis of the second signal 22 yields a quality factor denoted FS2.

The control unit further performs a correlation calculation to be detailed below, the output of this correlation calculation providing a third signal (third channel) which undergoes an analysis similar to that described above and which yields a third quality factor denoted FS3.

Depending on the period observed and the quality factor ('quality index') respectively calculated for each of the first, second, and third signals, the control unit selects the channel of the measurement believed to be the most reliable and displays the heart rate measured using this channel.

Instead of choosing the channel of the first or second signal after the fact, it would be possible to select in real time the best signal available between the two signals whenever an extremum is detected, the goal being to display the heart rate after a delay of about 5 to 10 seconds, preferably before 8 seconds.

Figure 7:
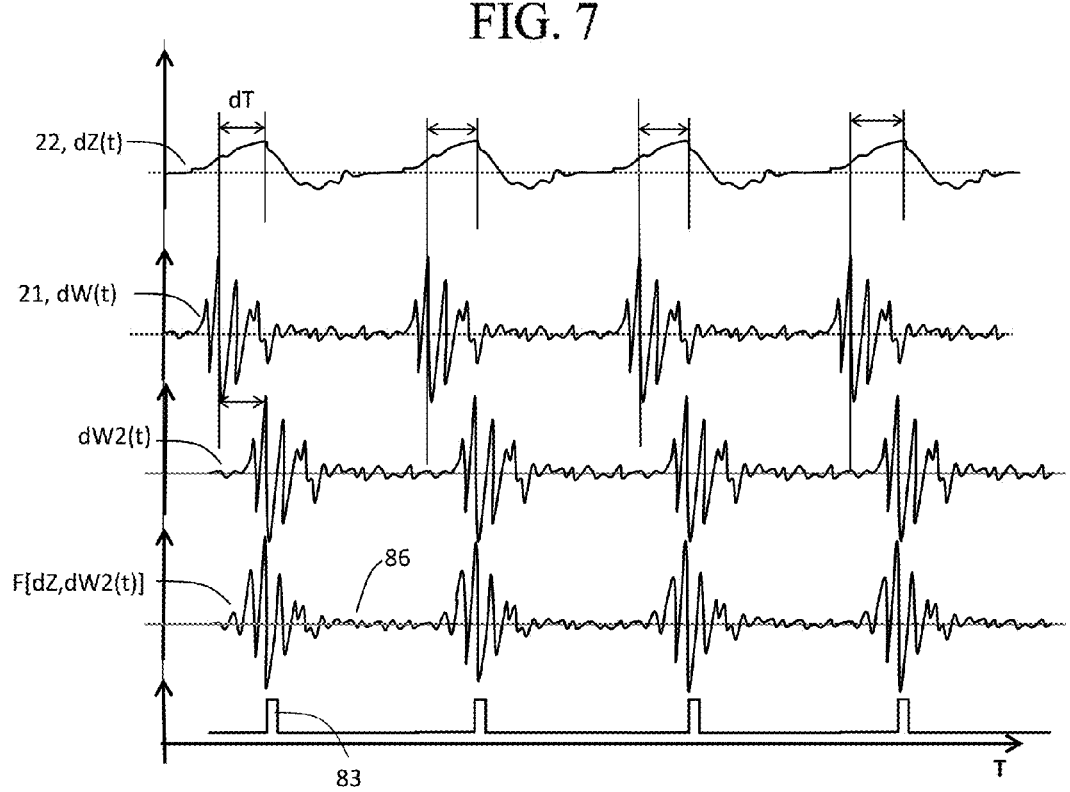

As illustrated in FIG. 7, for the correlation calculation a timing adjustment may first be applied to the first signal relative to the second signal or vice versa.

First, the control unit evaluates a phase difference denoted dT, by means of the relative position of the respective maxima of the first signal and second signal.

Next, one of the signals, in this example the first signal 21, is delayed by a time value dT so that the respective maxima of the signals are synchronized, as illustrated by signal dW2.

The control unit 4 then performs a correlation calculation, which consists of an arithmetic operation performed on the first and second signals of the signals, an operation denoted F[dZ,dW2]. For example, one can choose to multiply the signals together, add the signals, or perform some other operation that is the most relevant based on test runs performed on a large sample of individuals within a population. This can be referred to as a correlation or cross-correlation calculation.

In the resulting signal 86, the noisy portions of the first and second signals tend to cancel out statistically, while the useful portions of the signals tend to be strengthened.

From this cross-correlation signal 86, the control unit determines the aforementioned third pulse signal 83, which in the general case is more robust against the various unknowns and coverage deficiencies for all individuals in the population.

It should be noted that the evaluation of a quality index as described above can also be applied to the third signal from the correlation calculation; one can thus choose one of the three signals, especially if the correlation calculation proves not to be of good quality.

According to another variant, by using the computing power available in the electronic unit, it is possible to carry out recursive cross-correlation calculations, each time slightly shifting one signal relative to the other, without having to pre-evaluate dT. The signal having the highest average is then chosen from among the set of signals resulting from the cross-correlation calculations. In practice, this will correspond to the time covered by the significant portions of the signals. Conversely, if the significant portions of the signals do not overlap, then the multiplication gives a result near zero, because a significant signal is multiplied by noise.

One can thus consider improving the response time to less than 5 seconds or possibly even less than 4 seconds.

As an illustrative example, statistical test runs were conducted on several dozen people; failure was defined as an error of more than 10% compared to the heart rate measured by a reference device placed on the finger (PPG). Using only the measurement of weight variations, a failure rate of 23% was obtained; using only the measurement of impedance variations, a failure rate of 9.6% was obtained; using only the correlation of the two signals as explained above, a failure of 14% was obtained. By selecting the best of the three techniques (weight/impedance/correlation) based on the quality factors FS1, FS2, FS3, the overall failure rate can be reduced to 3.8% or even further; such a result cannot be achieved using only one of the first and second signals 21,22.

Figure 9:
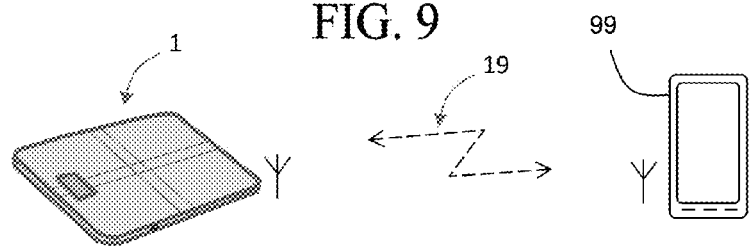
FIG. 9 shows a diagram of a system integrating the weighing device of FIG. 1.

FIG. 9 illustrates the integration of the digital bathroom scale 1 into a system for monitoring and tracking physiological data. In this system, the digital scale 1 can transmit data over a wireless link 19 to a smartphone 99 or a computer; daily data can thus be accumulated and displayed with statistical tracking for one or multiple users of the digital scale 1.

The method implemented in the scale can be summarized as follows:

a—a first signal 21 indicative of the periodic variations in weight caused by the user's heartbeats is measured, b—a second signal 22 indicative of the periodic variations in impedance caused by the user's heartbeats is measured, c—the user's heart rate is determined from the first and second signals.

Step c may make use of cross-correlation calculations, either recursive or simplified by first applying a temporal adjustment of the two signals relative to each other.

Finally, the control unit is configured to host the electronics for processing of the CO2 concentration sensor, and for correcting the obtained results transmitted by this sensor by means of calibration parameters or parameters related to the circumstances of use (humidity, altitude, etc.). The CO2 concentration may be displayed, and may be sent to remote processing means 99 as mentioned above.

More specifically, the CO2 concentration sensor is, for example, an NDIR (nondispersive infrared) sensor in which the absorption of infrared radiation by the presence of CO2 molecules within a cavity traveled by said infrared radiation is measured. In the current example, the maximum CO2 absorption is at wavelength $\lambda$=4.26 microns for a first channel measuring the absorption rate of infrared radiation. Preferably, a second measurement channel is used (a 'reference' channel), for example at a different frequency where the absorption by CO2 gas is negligible. Advantageously, measurements for the first channel and the second channel are compared to eliminate aberrations, particularly the aging of the radiation source and of the cavity itself (fouling).

The CO2 concentration sensor is connected to the control unit by a multi-wire connection 70, by means of which the control unit 4 intermittently controls the light source and captures the signals from the sensors for the first and second measurement channel.

Thus, the functionality of controlling the CO2 concentration sensor can be hosted in the electronic unit 4 which already performs the weighing and heart rate measurement functions, such that the integration of the CO2 measurement function is particularly advanced.

Furthermore, the dimensions of the CO2 concentration sensor have been adapted for integration within a digital bathroom scale. In the current example, the CO2 concentration sensor 7 is in the form of a tube of a diameter smaller than 10 mm (preferably less than 8 mm) and of a length less than 10 cm. A communication 71 with the outside air may further be provided, to allow sufficient exchange between the air in the cavity and the air in the immediate vicinity of the scale.

The control unit 4 is configured to trigger a measurement of the CO2 concentration periodically, for example every 10 minutes or every 30 minutes, or at intervals which may depend on the time of day or night.

Many digital scales are used in the bedroom; in this case, the digital scale generally remains in this room, and is thus used with its CO2 concentration sensor to monitor changes in CO2 concentration during the night. In addition, it can be arranged so that these data are sent from the digital scale to a remote computer or smartphone for statistical purposes, in a manner similar to that for the heart rate.

It is conceivable to calculate a correlation between the measured heart rate for a user when getting out of bed and the overnight history of CO2 concentration.

Aside from determining the heart rate by the method described above, it is also possible to use the measured signals to determine heart rate variability. Several signal periods are used to do so; the heart rate is determined as the average of the periods observed, while the heart rate variability is determined by a standard deviation from that average.

The invention claimed is:

1. A digital scale, comprising at least one strain gauge, at least two conducting portions arranged on a top surface of the scale, and an electronic control unit,
    the strain gauge being connected to the electronic unit and the electronic unit being configured to determine the weight of a user positioned on the weighing device, and to measure a first signal indicative of the periodic variations in weight caused by the heartbeats of the user,
    the conducting portions being connected to the electronic unit and the electronic unit being configured to measure an impedance at the user's feet and to measure a second signal indicative of the periodic variations in impedance caused by the heartbeats of the user,
    wherein the electronic unit is configured to evaluate a quality index for the first signal and a quality index for the second signal, and to determine the heart rate from the signal having the best quality index.

2. The weighing device according to claim 1 comprising four conducting portions, wherein the electronic unit is configured to inject a modulated or pulsed current between two of the conducting portions and to measure the electric potential difference between the two other conducting portions, in order to determine the variations in electric potential difference and thus determine the second signal.

3. The weighing device according to claim 1, wherein the electronic unit is configured to perform a cross-correlation calculation on the first and second signals.

4. The weighing device according to claim 3, wherein the electronic unit is configured to measure a phase difference (dT) between the first and second signals, and to shift the second signal relative to the first signal by said phase difference so that the cross-correlation calculation eliminates noise and maximizes the useful signal portions.

5. A digital scale, comprising at least one strain gauge, at least two conducting portions arranged on a top surface of the scale, and an electronic control unit,
    the strain gauge being connected to the electronic unit and the electronic unit being configured to determine the weight of a user positioned on the weighing device, and to measure a first signal indicative of the periodic variations in weight caused by the heartbeats of the user,
    the conducting portions being connected to the electronic unit and the electronic unit being configured to measure an impedance at the user's feet and to measure a second signal indicative of the periodic variations in impedance caused by the heartbeats of the user,
    wherein the electronic unit is configured to perform a cross-correlation calculation on the first and second signals, so to give a third signal,
    wherein the electronic unit is configured to evaluate a quality index for the first signal, a quality index for the second signal and a quality index for the third signal,
    wherein the electronic unit is configured to determine the heart rate from the first, second and third signals by choosing the one of the three having the highest quality index.

6. The weighing device according to claim 1, comprising four feet and four corresponding strain gauges, combined into two Wheatstone bridges, to allow the electronic unit to measure a user's weight and weight variations.

7. A Method implemented in a digital scale comprising at least one strain gauge, at least two conducting portions arranged on a top surface, and an electronic control unit,
    the strain gauge and the conducting portions being connected to the electronic unit to enable the electronic unit to measure the weight of a user positioned on the weighing device and an impedance at the terminals of the user's feet,
    the method comprising the steps of:
    a—measuring a first signal indicative of the periodic variations in weight caused by the heartbeats of the user,
    b—measuring a second signal indicative of the periodic variations in impedance caused by the heartbeats of the user,
    c—evaluating a quality index for the first signal and a quality index for the second signal, and
    d—determining the heart rate from the signal having the best quality index.

8. The method according to claim 7, wherein the device comprises four conducting portions, said method comprising during step b:
    injecting a pulsed current between two of the conducting portions and measuring the electric potential difference between the two other conducting portions, in order to determine the variations in electric potential difference and thus determine the second signal.

9. The method according to claim 7, further comprising in step c:
    performing at least one cross-correlation calculation on the first and second signals.

10. The method according to claim 9, further comprising in step c:
    measuring a phase difference between the first and second signals, and shifting the second signal relative to the first signal by said phase difference, so that the cross-correlation calculation eliminates noise and maximizes the useful signal portions.

11. The weighing device according to claim 5, wherein the electronic unit is configured to measure a phase difference (dT) between the first and second signals, and to shift the second signal relative to the first signal by said phase difference so that the cross-correlation calculation eliminates noise and maximizes the useful signal portions of the third signal.

* * * * *